United States Patent
Rothbrust et al.

(10) Patent No.: US 11,793,613 B2
(45) Date of Patent: Oct. 24, 2023

(54) PROCESS FOR THE PRODUCTION OF A DENTAL RESTORATION

(71) Applicant: Ivoclar Vivadent AG, Schaan (LI)

(72) Inventors: Frank Rothbrust, Röns (AT); Bo Jiang, Werdenberg (CH); Rudolf Jüssel, Feldkirch (AT); Christian Ritzberger, Grabs (CH)

(73) Assignee: Ivoclar Vivadent AG, Schaan (LI)

( * ) Notice: Subject to any disclaimer, the term of this patent is extended or adjusted under 35 U.S.C. 154(b) by 798 days.

(21) Appl. No.: 16/673,076

(22) Filed: Nov. 4, 2019

(65) Prior Publication Data
US 2020/0170765 A1 Jun. 4, 2020

(30) Foreign Application Priority Data
Nov. 29, 2018 (EP) ................... 18209308

(51) Int. Cl.
| | |
|---|---|
| A61C 13/00 | (2006.01) |
| A61C 13/083 | (2006.01) |
| C04B 35/48 | (2006.01) |
| C04B 35/645 | (2006.01) |
| A61C 5/77 | (2017.01) |
| C04B 35/64 | (2006.01) |
| A61C 13/08 | (2006.01) |
| A61K 6/818 | (2020.01) |

(52) U.S. Cl.
CPC .............. *A61C 13/082* (2013.01); *A61C 5/77* (2017.02); *A61C 13/0006* (2013.01); *A61C 13/083* (2013.01); *A61K 6/818* (2020.01); *C04B 35/48* (2013.01); *C04B 35/64* (2013.01); *C04B 35/645* (2013.01); *A61C 2201/002* (2013.01); *C04B 2235/3246* (2013.01); *C04B 2235/6562* (2013.01); *C04B 2235/6567* (2013.01); *C04B 2235/6581* (2013.01); *C04B 2235/6583* (2013.01); *C04B 2235/661* (2013.01); *C04B 2235/9661* (2013.01)

(58) Field of Classification Search
CPC .... C04B 2235/6581; C04B 2235/6583; C04B 2235/3246; A61C 13/0006; A61C 13/083
See application file for complete search history.

(56) References Cited

U.S. PATENT DOCUMENTS

| | | | |
|---|---|---|---|
| 5,984,683 A | 11/1999 | Sakata et al. | |
| 8,683,692 B2 | 4/2014 | Hayashi et al. | |
| 8,845,951 B2 | 9/2014 | Maginnis et al. | |
| 10,260,811 B2 | 4/2019 | Rohner et al. | |
| 2008/0303181 A1* | 12/2008 | Holand ............... | C04B 35/6264 264/16 |
| 2009/0029321 A1* | 1/2009 | Hayashi ................ | A61C 8/005 433/201.1 |
| 2011/0318582 A1* | 12/2011 | Dittmann ................ | C04B 41/80 501/134 |
| 2012/0058883 A1 | 3/2012 | Yamashita | |
| 2017/0128174 A1 | 5/2017 | Mayr et al. | |
| 2017/0176103 A1 | 6/2017 | Fornoff et al. | |
| 2017/0349494 A1 | 12/2017 | Yamashita et al. | |

FOREIGN PATENT DOCUMENTS

| | | |
|---|---|---|
| EP | 2098183 A1 | 9/2009 |
| EP | 2101133 A1 | 9/2009 |
| EP | 2703760 A1 | 3/2014 |
| WO | 20110020688 A1 | 2/2011 |
| WO | 2012057829 A2 | 5/2012 |
| WO | 2015091744 A1 | 6/2015 |

OTHER PUBLICATIONS

Extract from Yuezhu Li, Rapid Curing Technology and Material, National Defense Industry Press, Nov. 1993, p. 253 (Copy and English translation enclosed).

* cited by examiner

*Primary Examiner* — Erin Snelting
(74) *Attorney, Agent, or Firm* — Ann M. Knab; Thad McMurray

(57) ABSTRACT

The invention relates to a process for the production of a dental restoration, in which an oxide ceramic material
(a) is subjected to a first heat treatment,
(b) is subjected to a second heat treatment and
(c) is cooled,
wherein the heat treatment in step (a) is effected at lower pressure than the heat treatment in step (b).

15 Claims, No Drawings

PROCESS FOR THE PRODUCTION OF A DENTAL RESTORATION

CROSS-REFERENCE TO RELATED APPLICATIONS

This application claims priority to European patent application No. 18209308.8 filed on Nov. 29, 2018, the disclosure of which is incorporated herein by reference in its entirety.

TECHNICAL FIELD

The present invention relates to a process which, starting from an oxide ceramic material, makes it possible to produce a dental restoration with excellent properties in a short time. The invention also relates to the use of an oxide ceramic material for the production of a dental restoration by means of the process according to the invention.

BACKGROUND

Ceramic materials such as oxide ceramics are often used for the production of fully anatomical dental restorations. These offer high clinical safety, are usually metal-free, can also be used in minimally invasive preparations and are very attractive in terms of price in comparison with other metal-free restorations. However, a disadvantage is the numerous work steps which are usually necessary for the production of such restorations.

The restorations are usually milled or ground out of presintered blanks, optionally coloured, densely sintered by thermal treatment and finally optionally further coloured, glazed and/or polished.

Conventional processes for sintering dental ceramics include a slow heating-up to a maximum temperature, at which the oxide ceramic material used is densely sintered. Due to the low heating-up rate, such a sintering process typically takes much longer than hours and thus makes a significant contribution to an unsatisfactorily long duration of the production cycle of dental ceramics, in particular in the case of chairside treatments.

Approaches for accelerating the sintering process by increasing the heating rate are known in principle.

Thus EP 2 098 188 A1 and corresponding U.S. Pat. No. 10,260,811, which is hereby incorporated by reference, describe a dental furnace and a method for sintering dental materials in which the furnace is heated up in a first heating-up period at a rapid heating-up rate of more than 50 K/min to a presintering temperature of at least 1000° C.

EP 2 101 133 A1 describes a sintering furnace and a method for sintering dental preparations in which the dental preparations are moved along a sintering section and here are exposed to different temperatures. In a first segment, high heating-up rates of 300 K/min or more can be used.

WO 2012/057829 A2 and corresponding U.S. Pat. No. 10,260,811, which is hereby incorporated by reference, describe a method for rapidly sintering ceramic using electromagnetic induction or a plasma.

WO 2015/091744 A1 and corresponding U.S. Pat. No. 8,845,951, which is hereby incorporated by reference, describe a method for planning a sintering of a dental prosthesis part in which a temperature profile for the heat treatment of the dental prosthesis part is automatically determined by means of a computer as a function of specific geometric and material parameters of the dental prosthesis part to be produced. A heating rate between 100 K/min and 400 K/min is used for the sintering of particular dental prosthesis parts.

WO 2015/121364 A1 and corresponding US US2017176103, which is hereby incorporated by reference, describe a sintering furnace for dental components with a heating device which makes possible a heating rate of at least 200 K/min in the useful area.

The sintering of dental materials under protective gas or in a vacuum is also known.

WO 2011/020688 A1 describes a device for the oxygen-free sintering of metal or ceramic under protective gas in dental technology.

EP 2 703 760 A1 describes a dental furnace for sintering a dental prosthesis, the heating chamber of which can be closed either by means of a conventional closure device such as, for example, a door or by means of an attachment with a vacuum container and can thereby be used either for normal sintering or for vacuum sintering.

However, it has been shown that the known approaches for accelerating the sintering process lead to ceramic materials, the properties of which do not meet the high demands in the dental field, in particular relative to optical properties.

SUMMARY

The object of the invention is therefore to provide a process for the production of a dental restoration, by which dental restorations with excellent mechanical and in particular optical properties can be produced in a short time by sintering oxide ceramic material.

DETAILED DESCRIPTION

This object is achieved according to the invention by the process for the production of a dental restoration according to the claims. A subject of the invention is also the use of an oxide ceramic material for the production of a dental restoration according to the claims.

The process according to the invention for the production of a dental restoration is characterized in that an oxide ceramic material
(a) is subjected to a first heat treatment,
(b) is subjected to a second heat treatment and
(c) is cooled,
wherein the heat treatment in step (a) is effected at lower pressure than step (b).

Surprisingly, it was found that the process according to the invention makes possible a very rapid sintering of oxide ceramics to form dental restorations which have good mechanical properties and in particular a high density and at the same time also meet the high demands on dental restorations from an aesthetic point of view and can superbly imitate the optical properties of natural tooth material.

The oxide ceramic material used in step (a) is usually a non-densely sintered and in particular a presintered oxide ceramic material. The oxide ceramic material employed has usually a relative density in the range of from 30 to 90%, in particular in the range of from 40 to 80% and preferably in the range of from 50 to 70%, in each case relative to the true density of the oxide ceramic material.

The relative density is the ratio of the apparent density of the oxide ceramic material to the true density of the oxide ceramic material.

The apparent density of the oxide ceramic material can be calculated by means of the immersion method in accordance with ISO 18754 from the mass of the dry sample ($m_t$), the apparent mass of the sample immersed in an immersion liquid ($m_i$) and the density of the immersion liquid ($\rho_i$) according to the formula $$\rho = \frac{m_t}{m_t - m_i} \times \rho_i.$$

Carbon tetrachloride ($CCl_4$) is preferably used as immersion liquid.

The true density of the oxide ceramic material is determined by grinding the oxide ceramic material to a powder with an average particle size of from 10 to 30 μm, in particular of 20 μm, relative to the number of particles, and determining the density of the powder by means of a pycnometer. The determination of the particle size can be carried out, for example, with a CILAS® Particle Size Analyzer 1064 from Quantachrome GmbH & Co. KG using laser diffraction in accordance with ISO 13320 (2009).

In step (a) the oxide ceramic material is preferably heated to a temperature which lies in the range of from 1100 to 1600° C., in particular in the range of from 1200 to 1500° C., preferably in the range of from 1250 to 1450° C. and further preferred in the range of from 1300 to 1400° C. and is most preferred about 1350° C. It is further preferred that at the end of step (a) the oxide ceramic material has a relative density in the range of from 90 to 97%, in particular in the range of from 93 to 96% and preferably a relative density of about 95%, in each case relative to the true density of the oxide ceramic material.

In step (a) the oxide ceramic material is preferably heated up at a heating rate in the range of from 10 to 500 K/min, in particular 50 to 250 K/min and preferably 100 to 200 K/min. In a preferred embodiment, the oxide ceramic material is first heated up to a temperature which lies 100 to 700 K, in particular 200 to 450 K and preferably about 350 K below the maximum temperature reached in step (a) at a heating rate of from 50 to 500 K/min, in particular 100 to 250 K/min and preferably 150 to 200 K/min, and is then further heated up at a heating rate of from 10 to 200 K/min, in particular 25 to 150 K/min and preferably 50 to 100 K/min.

According to the invention, the heat treatment in step (a) is effected at lower pressure than the heat treatment in step (b). The heat treatment in step (a) is preferably effected at a pressure of less than 200 mbar, preferably less than 100 mbar and particularly preferred less than 50 mbar, and in particular at a pressure in the range of from 0.1 to 200 mbar, preferably in the range of from 1 to 150 mbar and particularly preferred in the range of from 50 to 100 mbar.

This pressure can be set at ambient temperature before the heating of the oxide ceramic material is begun. Alternatively, the oxide ceramic material can first be heated to a temperature above the ambient temperature before the pressure defined for step (a) is set. This temperature preferably lies in the range of from 20 to 500° C. and in particular in the range of from 25 to 100° C.

In step (b) the oxide ceramic material is preferably (b1) optionally further heated and (b2) held and sintered at a preferably constant temperature in the range of from 1100 to 1700° C., in particular in the range of from 1300 to 1600° C. and preferably in the range of from 1350 to 1550° C. and particularly preferred at a temperature of about 1500° C. The further heating in step (b1) is preferably effected at a heating rate of from 10 to 200 K/min, in particular 25 to 150 K/min and preferably 50 to 100 K/min. The holding in step (b2) is preferably effected for 1 to 60 minutes, in particular 2 to 30 minutes, preferably 3 to 15 minutes and particularly preferred about 5 minutes. By holding at the corresponding temperature the oxide ceramic material is typically densely sintered. After this the oxide ceramic material preferably has a relative density of at least 97%, in particular at least 98%, preferably at least 99% and most preferred at least 99.5%, in each case relative to the true density of the oxide ceramic material.

According to the invention, the heat treatment in step (b) is effected at higher pressure than the heat treatment in step (a). The heat treatment in step (b) is preferably performed at a pressure of more than 500 mbar and in particular at ambient pressure.

The heat treatment in step (b) is preferably effected in an oxygen-containing atmosphere. In particular air, oxygen-enriched air, and oxygen come into consideration as oxygen-containing atmosphere. In order to provide such an atmosphere, the heating chamber used for the heat treatment can be filled with air and/or oxygen. In a preferred embodiment, an oxygen-containing atmosphere, preferably air, oxygen-enriched air or oxygen flows through the heating chamber used for the heat treatment during step (b) discontinuously or preferably continuously, in particular at a flow rate of from 0.1 to 50 l/min, preferably 1 to 20 l/min and particularly preferred 4 to 8 l/min.

Moreover, it is preferred that in step (a) the oxide ceramic material is heated to a temperature which lies 0 to 500 K, in particular 10 to 250 K, preferably 50 to 200 K and particularly preferred 100 to 150 K below the temperature or the temperature range at or in which the oxide ceramic material is held in step (b).

Then in step (c) the oxide ceramic material is cooled. The oxide ceramic material is preferably cooled to a temperature which lies in the range of from 20 to 1300° C., in particular in the range of from 100 to 1250° C. and preferably in the range of from 1000 to 1200° C. After reaching such a temperature, the oxide ceramic material can be removed from the heating chamber. The cooling is preferably effected at a cooling rate of 50 to 200 K/min, in particular 75 to 175 K/min and preferably 100 to 150 K/min.

The oxide ceramic material obtained according to the process according to the invention preferably has a number-average grain size in the range of from 1 nm to 1000 nm, in particular from 10 nm to 800 nm and preferably from 100 nm to 600 nm. The number-average grain size can be determined in particular according to the linear intercept method in accordance with DIN EN 623-3 or ASTM E 112, wherein, for conversion to the actual number-average grain size in the three-dimensional microstructure, according to M. I. Mendelson, J. Am. Ceram. Soc. 1969, 52(8), 443-446, the determined value is multiplied by a proportionality constant of 1.56.

The process according to the invention is suitable for various types of oxide ceramic materials. Oxide ceramic materials are generally highly crystalline ceramic materials which are based on oxide compounds and at the most have a very low glass-phase portion. Typical oxide ceramic materials are based on $ZrO_2$, $Al_2O_3$, $TiO_2$, MgO, combinations, solid solutions or composites thereof, in particular $ZrO_2/Al_2O_3$ (ZTA), $Al_2O_3/ZrO_2$ (ATZ) or $ZrO_2$/spinel, wherein spinel is preferably Sr spinel, Mg spinel, La spinel and/or Ce spinel. Oxide ceramic materials based on $ZrO_2$ and/or $Al_2O_3$ are preferred according to the invention.

Oxide ceramic materials based on zirconia and in particular based on tetragonal zirconia polycrystal (TZP) are particularly preferred. Oxide ceramic materials based on zirconia, in which the zirconia is stabilized with $Y_2O_3$, $La_2O_3$, $CeO_2$, MgO and/or CaO and is preferably stabilized with 2 to 12 mol-%, in particular 3 to 5 mol-%, of these oxides, relative to the zirconia content, are quite particularly preferred.

It is further preferred that the oxide ceramic material is coloured. According to the invention, by this is meant an oxide ceramic material to which one or more colouring elements are added. Examples of suitable colouring elements are Fe, Mn, Cr, Pr, Tb, Er, Yb, Ce, Co, Ni, Nd, Cu and Bi. The oxide ceramic material particularly preferably comprises at least two layers which differ in their colour.

Within the meaning of the present application, the terms "colour" and "coloured" relate to the colour, lightness and/or translucence of a material.

"Translucence" is the light transmission of a material, body or layer, i.e. the ratio of transmitted to incident light intensity.

Colours can also be characterized by the colour coordinates $L^*$, $a^*$ and $b^*$ in the $L^*a^*b^*$ colour space or by a colour code usually used in the dental industry. In the $L^*a^*b^*$ colour space, the value $L^*$ describes the lightness of a colour with values of from 0 (black) to 100 (white), the value $a^*$ describes the green or red component of a colour, wherein negative values represent green and positive values represent red, and the value $b^*$ describes the blue or yellow component of a colour, wherein negative values represent blue and positive values represent yellow. Examples of colour codes usual in the dental industry are Vitapan Classical® and Vita 3D Master®, both from VITA Zahnfabrik H. Rauter GmbH & Co. KG, and Chromascop® from Ivoclar Vivadent AG. The translucence can be characterized by the contrast ratio CR, wherein 0% means completely transparent and 100% means completely opaque.

Usually, the colour coordinates $L^*$, $a^*$ and $b^*$ are determined according to DIN 5033 and DIN 6174 and the translucence is determined according to BS 5612. The corresponding measurements can be carried out in particular by means of a spectrophotometer of the CM-3700d type (Konica-Minolta). For this, test pieces are used for the measurements which have been wet-ground on both sides with diamond particles (particle size 15-20 µm) in order to obtain a final sample thickness of 2.00±0.025 mm.

The colour or colours of the dental restoration obtained according to the invention is/are preferably in the range of colours of natural teeth. Particularly preferably, the dental restoration obtained according to the invention has an $L^*$ value in the range of from 50 to 100, in particular in the range of from 80 to 97, an $a^*$ value in the range of from −10 to 10, in particular in the range of from −1 to 5, a $b^*$ value in the range of from 0 to 50, in particular in the range of from 1 to 20, and/or a CR value in the range of from 50 to 100%, in particular in the range of from 75 to 99%.

The process according to the invention is particularly suitable for the production of dental restorations. Particularly preferred dental restorations are bridges, inlays, onlays, crowns, veneers, facets and abutments. The process according to the invention is quite particularly suitable for the production of dental restorations, in particular bridges, which comprise two or more units.

The invention also relates to the use of an oxide ceramic material for the production of a dental restoration, in which the oxide ceramic material
(a) is subjected to a first heat treatment,
(b) is subjected to a second heat treatment and
(c) is cooled, wherein the heat treatment in step (a) is effected at lower pressure than the heat treatment in step (b).

Preferred embodiments of the use are as described above for the process according to the invention.

The invention is explained in more detail in the following with reference to examples.

EXAMPLES

General Procedure: Production of Test Pieces

Test pieces with a height of 17 mm, a width of 15.5 mm and a thickness of 2.5 to 3.5 mm were produced from commercially available blocks or discs of oxide ceramic by dry sawing using a diamond saw. After the sawing, the test pieces were dried in a drying cabinet at 80° C. for 2 h.

Example 1A

A test piece obtained in accordance with the general procedure from commercially available oxide ceramic blocks based on zirconia containing 3 mol-% $Y_2O_3$ (IPS e.max ZirCAD LT BL, Ivoclar Vivadent) was sintered in a sintering furnace with SiC heating element. For this, the test piece was introduced into the heating chamber of the sintering furnace at room temperature, the heating chamber was closed and a partial vacuum with a final pressure of about 50 to 100 mbar was generated in the heating chamber. The test piece was heated to a temperature of about 1000° C. at a heating rate of about 180 K/min and further to a temperature of about 1350° C. at a heating rate of about 80 K/min. Upon reaching this temperature, the heating chamber was flooded with fresh air and then fresh air flowed through continuously at a flow rate of about 5 l/min, while the test piece was further heated to a temperature of 1500° C. at a heating rate of about 80 K/min, held at this temperature for about 5 minutes and then cooled to a temperature of about 1100° C. at a cooling rate of about 140 K/min. The heating chamber was then opened. The total duration of the sintering process was about 19.5 min.

Example 1B (Comparison)

Example 1A was repeated, wherein, however, no vacuum was generated, but instead fresh air flowed through the heating chamber continuously for the total duration of the sintering process at a flow rate of about 5 l/min.

Example 1C (Comparison)

A test piece obtained in accordance with the general procedure from commercially available oxide ceramic blocks based on zirconia containing 3 mol-% $Y_2O_3$ (IPS e.max ZirCAD LT BL, Ivoclar Vivadent) was sintered in a sintering furnace of the Programat CS4 type (Ivoclar Vivadent) using the program P2 without automatic predrying. Here, the test piece was heated from room temperature to about 900° C. at a heating rate of about 130 K/min, further to about 1035° C. at a heating rate of about 50 K/min and finally to about 1460° C. at a heating rate of about 15 K/min. The test piece was held at this temperature for about 6 min and then cooled to a temperature of about 1200° C. at a cooling rate of about 70 K/min. The heating chamber was then opened. The total duration of the sintering process was about 47 min.

The density, translucence and colour coordinates of the oxide ceramic materials obtained in Examples 1A-C are reproduced in Table 1.

TABLE 1

| Example | Sintering duration [min] | Density [g/cm³] | CR [%] | L* | a* | b* |
|---|---|---|---|---|---|---|
| 1A | 19.5 | 6.065 | 88.99 | 95.87 | −0.37 | 1.75 |
| 1B (Comparison) | 19.5 | 6.066 | 92.54 | 96.14 | −0.31 | 1.81 |
| 1C (Comparison) | 47 | 6.068 | 88.53 | 95.79 | −0.27 | 1.96 |

They show that the process according to the invention according to Example 1A makes it possible to reach a density comparable with Examples 1B and 1C using a very short sintering duration of less than 20 min and at the same time to obtain a translucence which is comparable with the translucence obtained in the case of slow sintering according to Example 1C and is much higher than the translucence obtained in the case of fast sintering according to Example 1B.

Example 2

Test pieces obtained in accordance with the general procedure from commercially available oxide ceramic blocks based on zirconia containing 3 mol-% $Y_2O_3$ (IPS e.max ZirCAD LT BL B45 or IPS e.max ZirCAD LT A3 B45, Ivoclar Vivadent) or from commercially available oxide ceramic discs based on zirconia (Zenostar MT 3, Wieland Dental+Technik) were in each case sintered in a sintering furnace with $MoSi_2$ heating element. For this, the test pieces were introduced into the heating chamber of the sintering furnace at room temperature, the heating chamber was closed and a partial vacuum with a final pressure of <50 mbar was generated in the heating chamber. The test pieces were heated to a temperature of about 1050° C. at a heating rate of about 180 K/min and further to a temperature of about 1500° C. at a heating rate of about 80 K/min. In accordance with Table 2, upon reaching a temperature of 1350, 1400, 1450 or 1500° C., the heating chamber was flooded with fresh air and then fresh air flowed through continuously during the rest of the sintering process at a flow rate of about 5 l/min. The test pieces were held at a temperature of about 1500° C. for about 5 minutes and then cooled to a temperature of about 1100° C. at a cooling rate of about 140 K/min. The heating chamber was then opened.

For comparison, the above procedure was repeated, wherein, however, no vacuum was generated, but instead fresh air flowed through the heating chamber continuously for the total duration of the sintering process at a flow rate of about 5 l/min.

The density, translucence and colour coordinates of the oxide ceramic materials obtained in each case are reproduced in Table 2.

TABLE 2

| Material | Vacuum up to [° C.] | Density [g/cm³] | CR [%] | L* | a* | b* |
|---|---|---|---|---|---|---|
| IPS e.max ZirCAD LT BL B45 | 1350 | 6.072 | 91.06 | 95.48 | −0.39 | 2.70 |
| | 1400 | 6.075 | 89.98 | 95.44 | −0.41 | 2.95 |
| | 1450 | 6.077 | 89.04 | 95.38 | −0.48 | 3.01 |
| | 1500 | 6.075 | 88.05 | 94.95 | −0.47 | 3.25 |
| | no vacuum* | 6.070 | 92.35 | 96.06 | −0.25 | 1.85 |
| IPS e.max ZirCAD LT A3 B45 | 1350 | 6.079 | 96.66 | 82.78 | 4.76 | 17.89 |
| | 1400 | 6.080 | 96.96 | 83.12 | 4.55 | 17.45 |
| | 1450 | 6.081 | 94.14 | 81.31 | 5.41 | 18.34 |
| | 1500 | 6.078 | 97.62 | 83.59 | 3.80 | 16.37 |
| | no vacuum* | 6.070 | 97.29 | 84.82 | 3.77 | 16.34 |
| Zenostar MT 3 | 1350 | 6.041 | 98.83 | 86.13 | 1.53 | 14.73 |
| | 1400 | 6.041 | 98.34 | 87.21 | 1.14 | 14.11 |
| | 1450 | 6.048 | 96.93 | 83.93 | 2.23 | 15.91 |
| | 1500 | 6.044 | 98.71 | 86.16 | 1.48 | 15.65 |
| | no vacuum* | 6.033 | 99.50 | 86.96 | 1.27 | 14.45 |

*(Comparison)

Example 3

Test pieces obtained in accordance with the general procedure from commercially available oxide ceramic blocks based on zirconia containing 3 mol-% $Y_2O_3$ (IPS e.max ZirCAD LT A3 B45, Ivoclar Vivadent) or from commercially available oxide ceramic discs based on zirconia (Zenostar MT 3, Wieland Dental+Technik) were in each case sintered in a sintering furnace with $MoSi_2$ heating element. For this, the test pieces were introduced into the heating chamber of the sintering furnace at room temperature, the heating chamber was closed and in accordance with Table 3 a partial vacuum with a final pressure of 50, 100 or 200 mbar was generated in the heating chamber. The test pieces were heated to a temperature of about 1000° C. at a heating rate of about 180 K/min and further to a temperature of about 1350° C. at a heating rate of about 80 K/min. Upon reaching this temperature, the heating chamber was flooded with fresh air and then fresh air flowed through continuously at a flow rate of about 5 l/min, while the test pieces were further heated up to a temperature of 1500° C. at a heating rate of about 80 K/min, held at this temperature for about 5 minutes and then cooled to a temperature of about 1100° C. at a cooling rate of about 140 K/min. The heating chamber was then opened.

The densities of the oxide ceramic materials obtained in each case are reproduced in Table 3.

TABLE 3

| Material | Partial vacuum [mbar] | Density [g/cm³] |
|---|---|---|
| IPS e.max ZirCAD LT A3 B45 | 50 | 6.085 |
| | 100 | 6.084 |
| | 200 | 6.081 |
| Zenostar MT A3 | 50 | 6.052 |
| | 100 | 6.049 |
| | 200 | 6.048 |

Example 4

Test pieces obtained in accordance with the general procedure from commercially available oxide ceramic blocks based on zirconia containing 3 mol-% $Y_2O_3$ (IPS e.max ZirCAD LT BL B45 or IPS e.max ZirCAD LT A3 B45, Ivoclar Vivadent) or from commercially available oxide ceramic discs based on zirconia (Zenostar MT 3, Wieland Dental+Technik) were in each case sintered in a sintering furnace with SiC heating element. For this, the test pieces were introduced into the heating chamber of the sintering furnace at room temperature, the heating chamber was closed and a partial vacuum with a final pressure of about 50 to 100 mbar was generated in the heating chamber. The test pieces were heated to a temperature of about 1050° C. at a heating rate of about 180 K/min and further to a temperature of about 1500° C. at a heating rate of about 80 K/min. In accordance with Table 4, upon reaching a temperature of 1250, 1300 or 1350° C., the heating chamber was flooded with fresh air or oxygen which then flowed through continuously during the rest of the sintering process at a flow rate of about 5 l/min. The test pieces were held at a temperature of about 1500° C. for about 5 minutes and then cooled to a temperature of about 1100° C. at a cooling rate of about 140 K/min. The heating chamber was then opened.

For comparison, the above procedure was repeated, wherein, however, no vacuum was generated, but instead fresh air or oxygen flowed through the heating chamber continuously for the total duration of the sintering process at a flow rate of about 5 l/min in accordance with Table 4. In a further comparison, the above procedure was repeated, wherein, however, the partial vacuum with a final pressure of about 50 to 100 mbar was maintained for the total duration of the sintering process.

The density, average grain size, translucence and colour coordinates of the oxide ceramic materials obtained in each case are reproduced in Table 4.

TABLE 4

| Material | Vacuum up to [° C.] | Atmosphere | Density [g/cm³] | Average grain size [μm]** | CR [%] | L* | a* | b* |
|---|---|---|---|---|---|---|---|---|
| IPS e.max ZirCAD LT BL B45 | 1350 | Air | 6.066 | 0.396 ± 0.075 | 88.99 | 95.87 | −0.37 | 1.75 |
| | 1350 | $O_2$ | 6.057 | 0.375 ± 0.061 | 91.27 | 95.96 | −0.27 | 1.83 |
| | | continuously air* | 6.067 | 0.389 ± 0.077 | 92.54 | 96.14 | −0.31 | 1.81 |
| | | continuously $O_2$* | 6.047 | 0.386 ± 0.062 | 95.11 | 96.59 | −0.21 | 1.57 |
| IPS e.max ZirCAD LT A3 B45 | 1300 | Air | 6.088 | | 97.57 | 83.58 | 4.34 | 17.13 |
| | | continuously air* | 6.076 | | 98.34 | 83.72 | 4.23 | 17.02 |
| | | continuously $O_2$* | 6.065 | | 100 | 85.49 | 2.83 | 15.15 |
| Zenostar MT A3 | 1250 | Air | 6.052 | 0.584 ± 0.103 | 96.54 | 83.38 | 2.46 | 15.94 |
| | 1250 | $O_2$ | 6.052 | 0.543 ± 0.108 | 96.77 | 82.50 | 2.94 | 15.94 |
| | | continuously air* | 6.051 | 0.499 ± 0.131 | 98.31 | 84.93 | 1.57 | 14.04 |
| | | continuously vacuum* | 6.051 | 0.528 ± 0.097 | 97.64 | 82.01 | 0.09 | 12.05 |

*(comparison)

** The number-average grain size measured in accordance with DIN EN 623-3 was multiplied by 1.56 according to M. I. Mendelson, J. Am. Ceram. Soc. 1969, 52(8), 443-446 in order to obtain the actual number-average diameter in the three-dimensional microstructure.

The invention claimed is:

1. Process for the production of a dental restoration, which process comprises
   (a) subjecting a presintered oxide ceramic material to a first heat treatment comprising heating the oxide ceramic material to a temperature which lies in the range of from 1100 to 1600° C.,
   (b) subjecting the oxide ceramic material to a second heat treatment in an oxygen-containing atmosphere and
   (c) cooling the oxide ceramic material,
   wherein the heat treatment in step (a) is effected at lower pressure than the heat treatment in step (b).

2. Process according to claim 1, in which in step (a) the oxide ceramic material is heated to a temperature which lies in the range of from 1200 to 1500° C.

3. Process according to claim 1, in which in step (a) the oxide ceramic material is heated at a heating rate in the range of from 10 to 500 K/min.

4. Process according to claim 1, in which the heat treatment in step (a) is effected at a pressure of less than 200 mbar.

5. Process according to claim 1, in which in step (b) the oxide ceramic material is (b1) optionally further heated and (b2) held and sintered at a temperature in the range of from 1100 to 1700° C.

6. Process according to claim 5, in which the holding in step (b2) is effected for 1 to 60 minutes.

7. Process according to claim 5, in which in step (a) the oxide ceramic material is heated to a temperature which lies 0 to 500 K below the temperature or the temperature range at or in which the oxide ceramic material is held in step (b).

8. Process according to claim 1, in which the heat treatment in step (b) is effected at a pressure of more than 500 mbar.

9. Process according to claim 1, in which the heat treatment in step (b) is effected in air, oxygen-enriched air or oxygen.

10. Process according to claim 1, in which the oxygen-containing atmosphere flows through a heating chamber used for the heat treatment in step (b) discontinuously or continuously.

11. Process according to claim 1, in which in step (c) the oxide ceramic material is cooled to a temperature which lies in the range of from 20 to 1300° C.

12. Process according to claim 1, in which the oxide ceramic material is based on zirconia.

13. Process according to claim 12, in which the zirconia is stabilized with $Y_2O_3$, $CeO_2$, MgO and/or CaO.

14. Process according to claim 1, in which the oxide ceramic material is coloured.

15. Process according to claim 1, in which the dental restoration is a bridge, an inlay, an onlay, a crown, a veneer, a facet or an abutment.

\* \* \* \* \*